(12) United States Patent
Loughran (10) Patent No.: US 10,918,142 B2
(45) Date of Patent: Feb. 16, 2021

(54) SURGICAL AND INDUSTRIAL FACE MASK

(71) Applicant: William Loughran, Sea Girt, NJ (US)

(72) Inventor: William Loughran, Sea Girt, NJ (US)

( * ) Notice: Subject to any disclaimer, the term of this patent is extended or adjusted under 35 U.S.C. 154(b) by 0 days.

(21) Appl. No.: 16/442,857

(22) Filed: Jun. 17, 2019

(65) Prior Publication Data

US 2020/0121004 A1 Apr. 23, 2020

Related U.S. Application Data

(60) Provisional application No. 62/748,635, filed on Oct. 22, 2018.

(51) Int. Cl.
| | | |
|---|---|---|
| *A41D 13/11* | (2006.01) | |
| *A62B 18/02* | (2006.01) | |
| *A62B 23/02* | (2006.01) | |
| *A61M 16/06* | (2006.01) | |

(52) U.S. Cl.
CPC .......... *A41D 13/1107* (2013.01); *A62B 18/02* (2013.01); *A41D 13/1161* (2013.01); *A61M 16/0605* (2014.02); *A62B 23/025* (2013.01); *B01D 2239/065* (2013.01)

(58) Field of Classification Search
CPC .......... A41D 13/11–1192; A62B 18/00; A62B 18/02; A62B 18/025; A62B 18/08; A62B 18/084; A61M 16/00; A61M 16/06–0694; A61M 2205/02; A61M 2205/0216; A61M 2210/06; A61M 2210/0625
USPC ...................................... 128/206.12–207.13
See application file for complete search history.

(56) References Cited

U.S. PATENT DOCUMENTS

| | | | | |
|---|---|---|---|---|
| 3,664,335 A | * | 5/1972 | Boucher | A41D 13/113 128/206.19 |
| 3,974,829 A | | 8/1976 | Tate | |
| 4,037,593 A | | 7/1977 | Tate | |
| 4,635,628 A | | 1/1987 | Hubbard et al. | |
| 4,951,664 A | * | 8/1990 | Niemeyer | A62B 18/025 128/205.27 |

(Continued)

FOREIGN PATENT DOCUMENTS

| | | | | |
|---|---|---|---|---|
| GB | 2329340 A | * | 3/1999 | .......... A61M 16/047 |
| WO | 9740890 A2 | | 11/1997 | |

OTHER PUBLICATIONS

International Search Report PCT/US2019/056879 dated Feb. 6, 2020 (pp. 1-3).

*Primary Examiner* — Justine R Yu
*Assistant Examiner* — Matthew D Ziegler
(74) *Attorney, Agent, or Firm* — Law Office of Jeff Williams PLLC; J. Oliver Williams (57) ABSTRACT

A facial mask includes a foam sealer that is attached at one or more sides of the mask. The foam sealer prevents air or breath from going upwards out of the mask, thereby preventing glasses from being fogged up during surgery. It also keeps air or materials from getting into the mask and prevents, to a degree, bodily fluids and unwanted odors from penetrating the mask than existing masks. The mask prevents unwanted distractions to the surgeon or other medical personnel. The mask also may prevent medical illnesses from the inhalation of air, the exposure to bodily fluids, or the transfer of gases. The foam sealer is comprised of open cell foam. The facial mask acts as a more complete barrier to odors and bodily fluids that may otherwise endanger both the user or other personnel.

8 Claims, 9 Drawing Sheets

(56) References Cited

U.S. PATENT DOCUMENTS

| | | |
|---|---|---|
| 5,694,925 A | 12/1997 | Reese et al. |
| 5,735,270 A | 4/1998 | Bayer |
| 5,797,146 A | 8/1998 | Matich |
| 5,934,275 A | 8/1999 | Gazzara |
| 6,354,296 B1 | 3/2002 | Baumann et al. |
| 6,868,984 B2 * | 3/2005 | Griesbach, III ....... A41D 13/11 221/303 |
| 6,978,782 B2 * | 12/2005 | Tayebi ................. A62B 23/025 128/201.17 |
| 10,357,672 B2 * | 7/2019 | Bora ....................... A61F 9/028 |
| 2003/0221690 A1 * | 12/2003 | Lee ................... A61M 16/1075 128/206.12 |
| 2006/0174890 A1 | 8/2006 | Cheng |
| 2008/0023006 A1 * | 1/2008 | Kalatoor ................ A41D 13/11 128/205.29 |
| 2014/0332012 A1 * | 11/2014 | Mekler ............. A41D 13/1123 128/863 |
| 2017/0027251 A1 | 2/2017 | Kang |
| 2018/0160749 A1 | 6/2018 | Kim |

\* cited by examiner

SURGICAL AND INDUSTRIAL FACE MASK

FIELD OF THE INVENTION

The present invention relates a surgical and industrial face mask for use on the face of a person that prevents "fogging" of glasses or the creation of condensation on glasses during use. The mask also reduces abrasiveness of the materials during use and decreases the inhalation of odors.

DESCRIPTION OF THE RELATED ART

Masks are used to prevent the spread or receipt of germs or foul air in a variety of settings. For example, physicians and other medical personnel wear masks during surgery for a variety of reasons. These masks may be uncomfortable and abrasive. The surgical mask also causes the glasses of the physician to "fog up" where the breath of the wearer is diverted onto the surface of the glasses. Condensation may form which obstructs the view of the physician. The mask does not provide an adequate barrier or seal around its rim due to different facial structures and any facial hair. In other words, most surgical masks are "one size fits all" such that a seal is not formed on most operating room personnel.

During an operation, a doctor may stop four or five times to clean his/her glasses. Other times, the glasses are removed to be changed or cleaned by an assistant. This stoppage may take up to five minutes while a patient lies on the operating table. These delays pose medical risks to the patient due to longer exposure to possible bacteria and increased costs due to longer usage of the operating room. Sometimes, the doctor may not pause to clean the glasses and continue to perform surgery with them fogged up. This situation may lead to accidents or mishaps.

Existing facial masks may exhibit some negative characteristics. They are uncomfortable for most people. The masks are abrasive to delicate facial skin. As noted above, an adequate barrier is not provided to seal around the rim of the mask to prevent breath from being diverted upwards or to properly protect the face from contaminants. Existing masks also do not adequately prevent the fogging of glasses or the inhalation of odors.

Further, existing masks do not have any changeable properties. The masks cannot have materials within them that fight infection or odors without being in contact with the user's skin. One would have to rub medicine or other materials onto the mask, which may cause further slippage of the masks as well as possible deterioration of the material of the mask.

SUMMARY OF THE INVENTION

A facial mask is disclosed. The facial mask includes mask material having a shape. The facial mask also includes a foam sealer of open cell foam attached at the sides of the mask material with an adhesive or sewn thereto. The foam sealer is die cut to be a unitary piece that fits the mask material. The facial mask also includes ties extending from the sides of the mask material.

Another facial mask is disclosed. The facial mask includes mask material having a shape. The facial mask also includes a foam sealer of open cell foam attached to a side of the mask material with an adhesive or sewn thereto. The facial mask also includes ties extending from the sides of the mask material. A wire may be placed at the upper side of the mask for shaping the mask to one's facial contours.

Another facial mask is disclosed. The facial mask includes a first side and a second side. Each side has mask material having a shape. The mask materials of the sides are joined to form an opening enclosed by the first side and the second side. Each side of the facial mask has a foam sealer of open cell foam attached by an adhesive or sewn to the mask material at the border of the opening. Each side of the facial mask has a strip that hangs below the foam sealer. The facial mask also includes a bottom positioned opposite the opening. The bottom is shorter in length than the opening.

A facial mask is disclosed. The facial mask includes mask material having a shape. The facial mask also includes a foam sealer of open cell foam attached at the sides of the mask material. The foam sealer is die cut to be a unitary piece that fits the mask material. The facial mask also includes ties extending from the sides of the mask material.

A facial mask is disclosed. The facial mask includes mask material having a shape. The facial mask also includes a foam sealer of open cell foam attached to a side of the mask material with an attachment means. The foam sealer is configured to have a shape. The facial mask also includes ties extending from the sides of the mask material.

A facial mask is disclosed. The facial mask includes a first side and a second side. The facial mask also includes each side having mask material having a shape. The mask materials are joined to form an opening enclosed by the first side and the second side. The facial mask also includes each side having a foam sealer of open cell foam attached by attachment means to the mask material at the border of the opening. The facial mask includes each side having a strip that hangs below the foam sealer. The facial mask includes a bottom positioned opposite the opening. The bottom is shorter in length than the opening.

BRIEF DESCRIPTION OF THE DRAWINGS

Various other features and attendant advantages of the present invention will be more fully appreciated as the same becomes better understood when considered in conjunction with the accompanying drawings.

DETAILED DESCRIPTION OF THE PREFERRED EMBODIMENTS

Reference will now be made in detail to specific embodiments of the present invention. Examples of these embodiments are illustrated in the accompanying drawings. While the embodiments will be described in conjunction with the drawings, it will be understood that the following description is not intended to limit the present invention to any one embodiment. On the contrary, the following description is intended to cover alternatives, modifications, and equivalents as may be included within the spirit and scope of the appended claims. Numerous specific details are set forth in order to provide a thorough understanding of the present invention.

The present invention addresses the real-world concerns of physicians and medical personnel in the operating room or other hospital settings that seek to prevent inhaled exposure, the fogging of glasses, and penetration of bodily fluids. They find existing surgical masks to be abrasive and uncomfortable. Further, physicians are compelled to wear masks that do not adequately prevent the fogging of glasses or goggles as well as fails to provide an adequate barrier or seal around the rim of the masks, which also acts as a deterrent for odors and prevents the penetration of bodily fluids. The lack of a barrier or seal is especially prevalent with the wide range of facial structures and facial hair of users.

Facial masks also may be used in other settings. For example, masks may be used in construction settings where a user also wears protective glasses. The protective glasses also "fog up" so that the worker cannot adequately see what he or she is doing plus breaks to clean off the glasses. People also wear facial masks in public, especially in Asia, to prevent the spread or receipt of germs or to not breathe polluted air. The problems discussed above also pertain to these uses. Perspiration and air still get through to the mask and part of the face covered by the mask. Though the disclosed mask is described in a surgical or medical setting, it also may include embodiments related to other settings that require a mask that covers part of the face, especially the mouth and nose.

Surgical mask efficiency may be impaired by wearing masks too close to the nose because of the collection of moisture. Conventional surgical masks are designed to prevent the passage of relatively large particles, such as hair or sputum droplets. As opposed to addressing efficiency, the disclosed embodiments focus on the equally important goal of efficacy for facial masks. This feature relates directly to how the mask fits over a variety of head sizes and facial structures and how well it handles moisture issues. The dual goals of efficiency and efficacy are conflated often in a discussion of surgical masks to the detriment of the surgeon and the patient. Surgical masks primarily focus on the efficiency aspect while efficacy is not much more than an afterthought. This oversight places the mortality of the patient at high risk.

Resolution of both goals regard multiple issues. These issues may include filtration, fluid resistance to protect the surgeon from bodily fluid, features, such as the reduction of the fogging issue, and fit of covering the face. With regard to filtration, most surgical masks fail on several levels. They do not form a good seal around the rim, especially if the person wearing it has large facial features, a beard, or a moustache. Such a mask may not provide 100% efficiency to filter particles 0.3 microns or larger, roughly the size of a single virus. This consideration overlaps with the fit issue. Conventional mask may cause a rash due to the abrasiveness of the glue used.

Masks also may be relatively difficult to breathe through. They may be associated with feelings of claustrophobia and kind of a suffocating sensation. Surgical masks also experience 30 to 50% face seal leaks. The disclosed mask enhances the filtration of small particles by improving the fit while not altering the basic properties of masks. The foam sealer attached around the periphery of the mask functions as a filter for unwanted odors from bodily secretions during medical procedure activities. With regard to modifications to masks disclosed herein, the design of the facial mask is different than known masks. The foam sealer attached to the periphery of the mask forms a barrier to bodily fluids that can come into contact with the face of the user.

The disclosed embodiments include a foam sealer. The foam sealer prevents fogging of the eyewear during a medical procedure, work project, normal wear outside, and the like. Users may find that wearing masks allow odors, secretions that may come into contact with one's face, and fogging of eyewear during use. These distractions may interfere with a person's concentration while performing actions, such as surgery, construction, and the like. When the timing of the procedure is of the essence, these distractions may hurt the patient in a medical setting, especially if a surgeon loses his concentration or has to stop to change eyewear or mask, or to clean themselves from bodily secretions.

In some instances, the nose and mouth must be covered and a seal created around the face to prevent gaps that increase the risk of inhalation exposure for facial protection. Because of the lack of a tight seal, surgical masks may experience a 30 to 50% face seal leak. The disclosed mask is soft to the skin, not abrasive, and supports the existing wire at the superior rim of some surgical masks, thereby making it very easy to shape the mask around the nose to form a tight seal. The disclosed mask fits a variety of facial structures and faces with facial hair, beards and moustaches. Masks according to the disclosed embodiments increase comfort and reliability. They also eliminate the fogging of glasses so that a user does not need to halt what he or she is doing and make procedures safer for the user, patients, and co-workers.

The disclosed embodiments include at least two designs. A first design modifies existing masks with a layer of blue open cell foam glued or sewn around the whole rim. A second design may include the blue open cell foam glued or sewn at the upper or superior rim of the mask. Other designs also may be implemented according to the different embodiments of the invention.

The disclosed surgical masks address the shortcomings associated with conventional masks. The disclosed masks are soft to the face so as to prevent irritation of the skin and to promote comfort while being worn during surgery. Existing masks sometimes cause a rash (dermatitis) due to the abrasiveness of the material or glue used in the masks. This result is preventable with the thicker ½ inch open cell foam used in the disclosed mask. The cell foam may be glued or sewn around the mask. The thicker cell foam also acts as an improved barrier to germs and bodily fluids. Unlike conventional masks, the disclosed mask prevents these items from entering around the borders of the disclosed mask.

As noted above, conventional masks do not form a reliable seal around the rims. This aspect may be especially true if the person wearing the mask possesses broader or larger facial characteristics than normal or has a beard or mustache. The disclosed mask is sufficiently versatile to form a reliable seal in both of these instances.

For example, N-95 respirator masks, as currently used, do not form a reliable seal around the rim of the masks. This may be especially true if the person wearing the mask possesses broader or distinct facial characteristics from normal. Moreover, facial hair, such as a beard or moustache, also may prevent the formation of a reliable seal around the rim. The disclosed mask is sufficiently versatile to form a reliable seal under these scenarios.

Conventional surgical masks have the following characteristics at the upper or superior border of the mask: a flat-like foam surface, plastic or sticky adhesive, or a thin piece of metal. The flat foam masks do not adequately provide a barrier, thereby allowing warm air to escape and fog eyeglasses and unwanted odors to penetrate. They also do not deter unwanted bodily fluids from penetration. This can be a critical problem during a surgical procedure, where medical personnel use their hands to perform the procedure. The hands are covered with gloves. Adhesive masks do not stick well. Most of the time in real-life situations, they still allow glasses to fog and unwanted odors or bodily fluids that can be a distraction to the surgeon or other medical personnel.

The disclosed mask of the present invention supports the existing wire at the superior rim, which is present in some surgical masks. This feature makes it easy to shape the mask around the nose to form a tight seal. The tight seal may avoid any fogging of glasses due to the thicker open cell foam used in the disclosed embodiments.

Embodiments of the disclosed mask may be soft to the face and not liable to cause a rash. The disclosed mask also forms an effective seal to prevent fogging. The open cell foam glued around the total rim prevents bodily fluids from entering the facial skin and hair. Thus, a user does not have to become concerned that the sticky surface will become "unsticky" due to sweat during an extended period of wearing the mask. Surgeries often require an extended period of the user not being able to adjust or remove the mask. The thicker foam surgical mask stays on without any shifting of the mask. Further, it does not become loose due to the glue not sticking to the person's nose. Odors also may be deterred due to the seal that is less distracting to the surgeon or other medical personnel. The disclosed embodiments also prevent unwanted bodily fluids to penetrate.

In summary, the disclosed surgical mask alleviates the problems with conventional masks discussed above. It also increases comfort and reliability while eliminating the potentially dangerous condition of fogged glasses. This feature makes surgeries safer for many thousands of people on an annual basis. The surgeon, or other medical personnel, will not have to stop the surgery or operation to clean his/her glasses. It also decreases the penetration of odors and bodily fluids that may distract the surgeon's or other medical personnel's ability to work and makes it safer for the surgeon, medical personnel, and all involved.

The disclosed surgical masks incorporate high density memory foam. High density memory foam softens in reaction to body heat, thereby allowing it to mold or shape to a warm body. Some pieces of the foam will be die cut. It may be sewn on medical grade viscose plastic foam or use a medical grade adhesive, blue SIMALFA 321 (super instant tack high yielding and fast drying that is one part water base adhesive that may be used in a variety of applications).

Figure 1A:
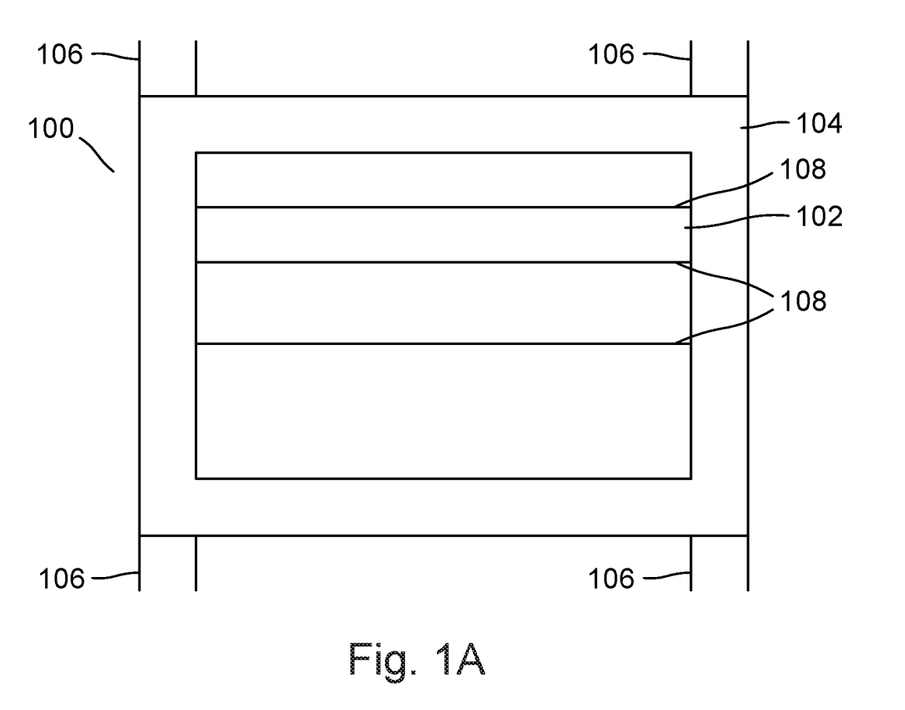
FIG. 1A illustrates a facial mask according to the disclosed embodiments.
Figure 1B:
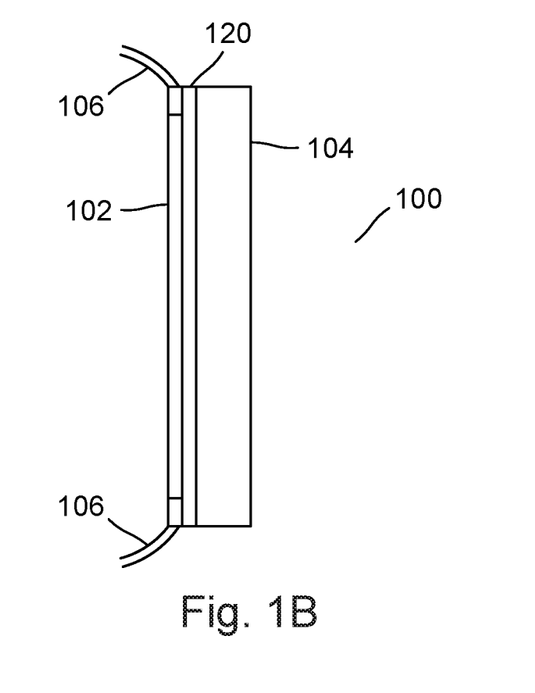
FIG. 1B illustrates a side view of the facial mask of FIG. 1A according to the disclosed embodiments.

FIG. 1A depicts a facial mask 100 according to the disclosed embodiments. FIG. 1B depicts a side view of facial mask 100 according to the disclosed embodiments. Facial mask 100 includes mask material 102. Facial mask 100 also be referred to as a surgical mask below. Mask material 102 may be a cloth material, preferably made of cotton or other fabric that allows air to flow through in some manner to the outside of mask 100 when worn on a face. Mask material 102 also may include one or more layers of material. Such material may include woven and nonwoven fabrics.

Facial mask 100 also includes foam sealer 104. Foam sealer 104 also may be known as a foam border for mask 100. Foam sealer 104 is attached to mask material 102, preferably using adhesive 120, as shown in FIG. 1B. The different types of adhesives applicable to facial mask 100 may be disclosed above. Foam sealer 104 preferably comprises open cell foam, which is softer and more pliable than other foams. In some embodiments, the open cell foam is blue open cell foam. Alternatively, foam sealer 104 may comprises closed cell foam. Foam sealer 104 is die cut to have a shape that fits surgical mask 100. Portions of mask material 102 or foam sealer 104 are not overlapping or hanging off the mask. In this embodiment, foam sealer 104 is attached to all the borders of mask material 102. It encompasses the shape of the mask.

Facial mask 100 also includes ties 106. Ties 106 may be strings or laces that extend away from the sides of surgical mask 100. In some embodiments, ties 106 may be flat. Ties 106 are shown extending from the top and bottom of facial mask 100, but also may extend from the sides. Facial mask 100 also includes creases 108 in mask material 102. The creases allow the mask material to expand or contract, as needed, when the mask is on a user. Although three creases 108 are shown, any number of creases may be placed into mask material 102. It is noted that foam sealer 104 is not on a crease and should not be impacted by creases 108 allowing for expansion of facial mask 100.

Figure 2A:
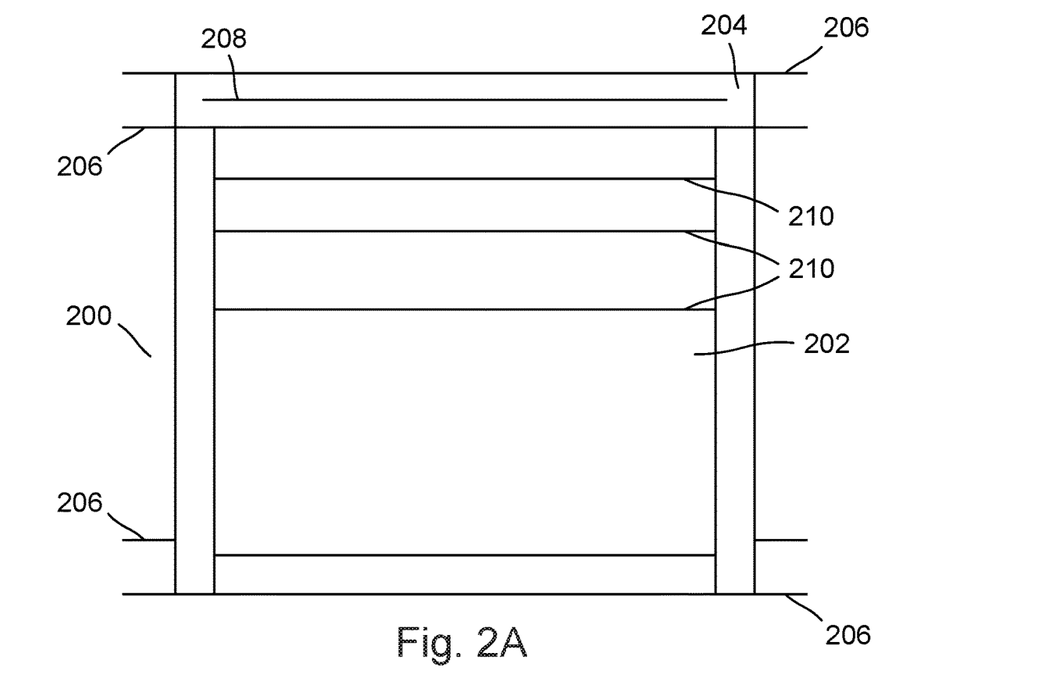
FIG. 2A illustrates a facial mask according to the disclosed embodiments.
Figure 2B:
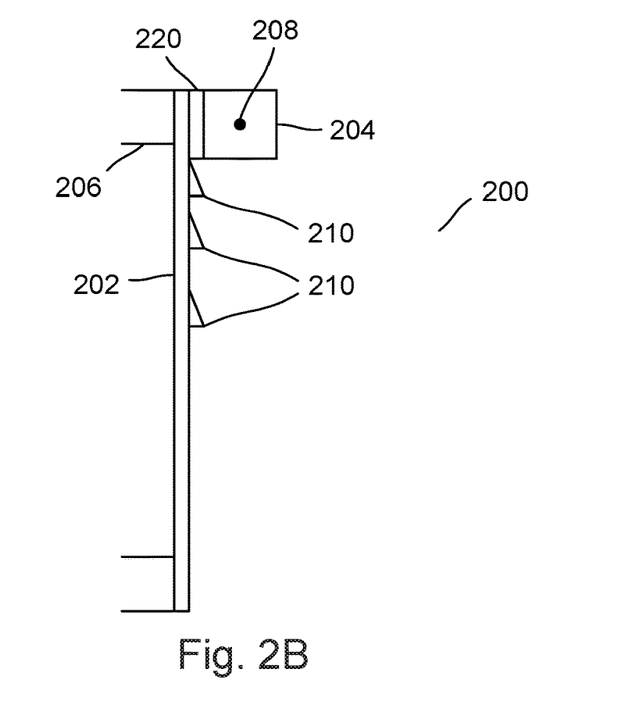
FIG. 2B illustrates a side view of the facial mask of FIG. 2A according to the disclosed embodiments.

FIG. 2A depicts another facial mask 200 according to the disclosed embodiments. FIG. 2B depicts a side view of facial mask 200 according to the disclosed embodiments. Facial mask 200 differs from facial mask 100 in that it has foam sealer 204 on one side of the mask. Foam sealer 204 also may be open cell foam that is attached to the upper, or superior, side of facial mask 200. On the other sides of facial mask 200, mask material 202 is exposed. Foam sealer 204 may be attached to mask material 202 with adhesive 220, which also is on one side of facial mask 200.

Facial mask 200 also includes ties 206, which function much like ties 106 disclosed above. Ties 206 are shown extending from the sides of facial mask 200. Ties 206 also may extend from the top and bottom of facial mask 200. As can be seen in FIGS. 2A and 2B, mask material 202 includes creases 210. Creases 210 function much like creases 108 disclosed above.

Facial mask 200 also includes a wire 208 that extends along the upper side of the mask. Wire 208 may be enclosed by foam sealer 204. In some embodiments, wire 208 may be surrounded by the foam of foam sealer 204. In other embodiments, wire 208 may be attached to mask material 202. Wire 208 bends to shape the top part of mask 200 to fit a face. Foam sealer 204 provides comfort from wire 208 touching or scratching the face of a user.

Figure 3A:
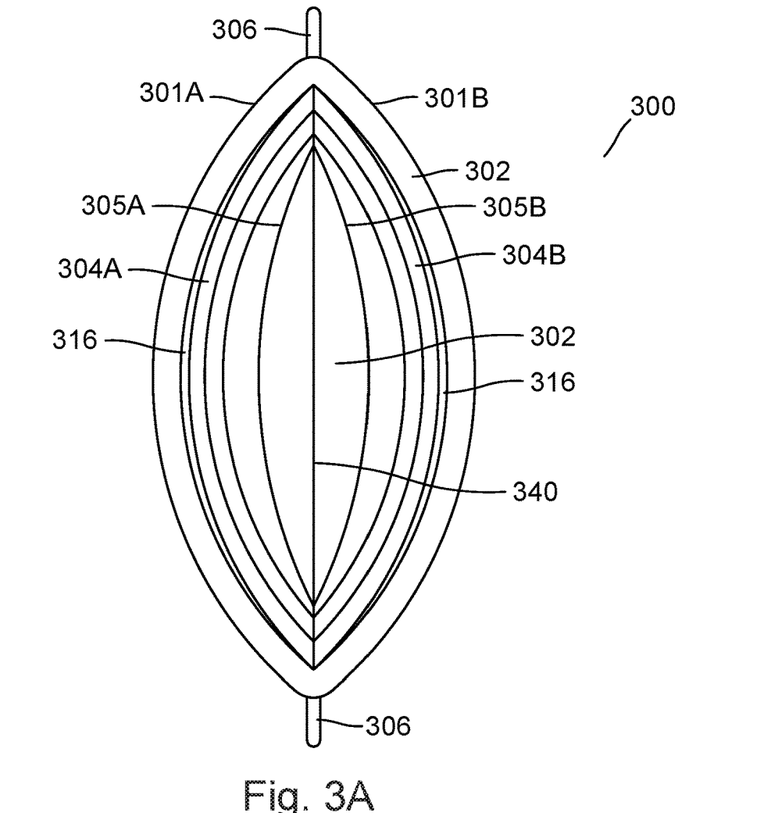
FIG. 3A illustrates a facial mask according to the disclosed embodiments.
Figure 3B:
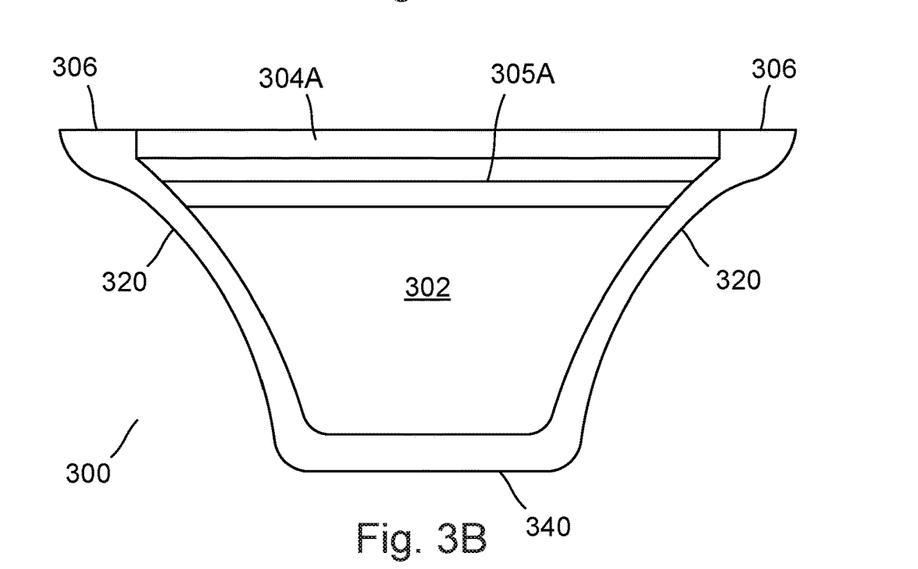
FIG. 3B illustrates another view of the facial mask of FIG. 3A according to the disclosed embodiment.

FIG. 3A depicts another facial mask 300 according to the disclosed embodiments. FIG. 3B depicts a cut away side view of facial mask 300 according to the disclosed embodiments. Mask 300 differs from the other masks in that it has two sides 301A and 301B. The sides may be symmetrical such that each side has the same shape. Sides 301A and 301B may be defined by mask material 302. Mask material 302 envelopes the other components of facial mask 300.

Facial mask 300 also includes foam sealers 304A and 304B that line the inner sides of mask material 302. Facial mask 300 uses two portions of foam sealers. The two pieces may be die cut as well. Foam sealers 304A and 304B are in contact at the upper and lower portions of surgical mask 300. Foam sealers 304A and 304B are attached to mask material 302 by adhesive 316.

Strips 305A and 305B also are attached to mask material 302, but only at the top and bottom parts of facial mask 300. The remaining portions of strips 305A and 305B hang loose within the opening of facial mask 300. Strips 305A and 305B may lie against the face of a user. The strips may be positioned below foam sealers 304A and 304B. As shown in FIG. 3B, strip 305A is below foam sealer 304A, but it does not necessarily have to against the foam sealer throughout the length of the strip.

Bottom 340 of facial mask 300 shows where mask material 302 comes together and sides 301A and 301B are joined. This also occurs on the outer sides of facial mask 300, as shown by stitching border 320. Except for the opening encircled by foam sealers 304A and 304B, the outer sides of facial mask 300 are joined together. Tabs 306 also show where mask material 302 is joined together. Tabs 306 extend further out from stitching border 320 of facial mask 300.

Figure 6:
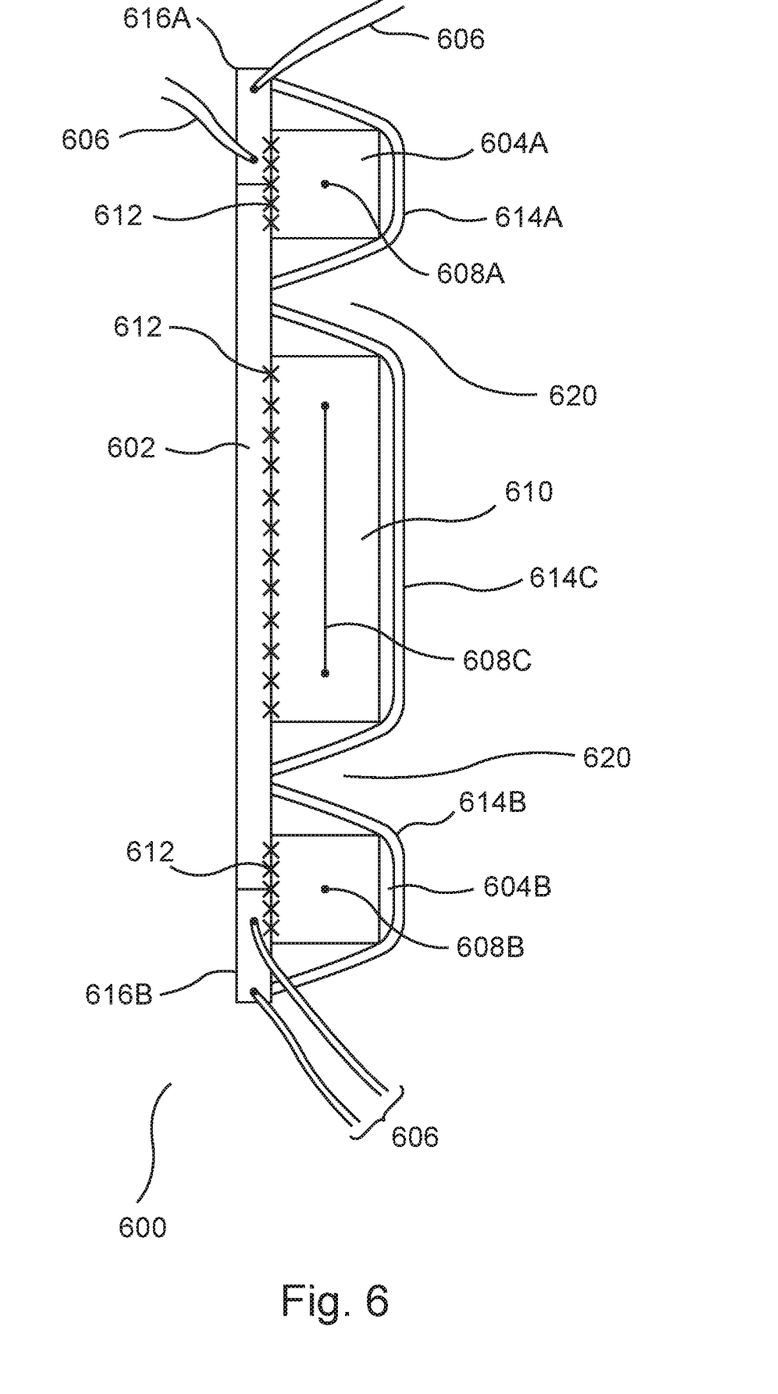
FIG. 6 depicts a side view of a facial mask having the foam sealers stitched therein according to the disclosed embodiments.

The adhesives shown in FIGS. 1A-3B are depicted larger than the strips for adhesives are for illustrative purposes. Adhesive should be used wherever foam sealers are attached to the mask material to form a mask. In other embodiments, the foam sealers may be incorporated into the manufacture of the facial mask, as opposed to being secured using an adhesive. As such, the foam sealer may be stitched onto the mask material. In other embodiments, the mask material may cover the foam sealer. These embodiments are shown in FIG. 6, disclosed below.

The mask material used in facial masks 100, 200, and 300 may form a shape. In some embodiments, the shape is a rectangle. In other embodiments, the mask material may have another shape, such as shown in FIGS. 3A and 3B. The shape of the mask material should relate to providing an adequate mask to cover the face of a user.

Facial mask 100, 200, and 300 disclosed above use open cell foam within the foam sealers. Open cell foam is made by incorporating an inflating agent, such as sodium bicarbonate, into the rubber compound. The agent gives off a gas, which expands the rubber during vulcanization. Foam may be called "open cell" when more than half of its cells are open. Open cell materials may include reticulated foam, polyurethane foam, and open cell rubber.

Some open cell foam is unique in that it operates to easily return to its original state after compression due to unrestricted air movement and chemical makeup. Soft and breathable, open cell foam is flexible and provides sealing capabilities for the facial mask. Open cell foam within the foam sealer allows it to fit on a variety of different facial structures and beards, mustaches, and the like. After use, the open cell foam in the foam sealer may return to its original shape so that it provides the same sealing properties during the next use. The open cell foam within the foam sealer may have a specific density that allows these properties to be used within the facial mask. Reticulated foam may be classified by pores per inch, or PPI. A 10 PPI foam would have large cell structures and allow the most flow of air while 80 PPI foam would have very small cells to be more restrictive. Preferably, the open cell foam within the foam sealer is about 75 to 85 PPI.

Medical grade open cell foam may include polyurethane and reticulated polyurethane foams. Reticulated polyurethane foams may be used for the foam sealer embodiments disclosed above. This type of foam allows easy cleaning, lack of susceptibility to microbial organisms, and may be made with fungicidal and bactericidal additives for added effectiveness during use. A reticulated polyurethane foam sealer also may be injected with substances to achieve other unique properties.

Closed cell foam also may be used in some embodiments for the foam sealer component of the facial mask. Closed cell foam may be a cell totally enclosed by its walls and not interconnecting with other cells. Closed cell foam may be made by subjecting a rubber compound to a gas, such as nitrogen, under high pressure. The foam also may be made by incorporating gas-forming materials into the compound. Closed cell foam offers a variety of material and density options, which can range from 6 $lb/ft^3$ (soft) to 19 $lb/ft^3$ (hard).

The disclosed embodiments also may use cross linked polyurethane foam in the closed cell foam sealer. Cross linked polyurethane may provide rigidity, durability, and performance. It has low moisture permeability and a high buoyancy rating. This type of foam also is resistant to wear and tear, mold, mildew, and bacteria. It also may be resistant to most chemicals and is nontoxic as well as free from CFCs, HCFCs, and hydrocarbon blowing agents.

Figure 4:
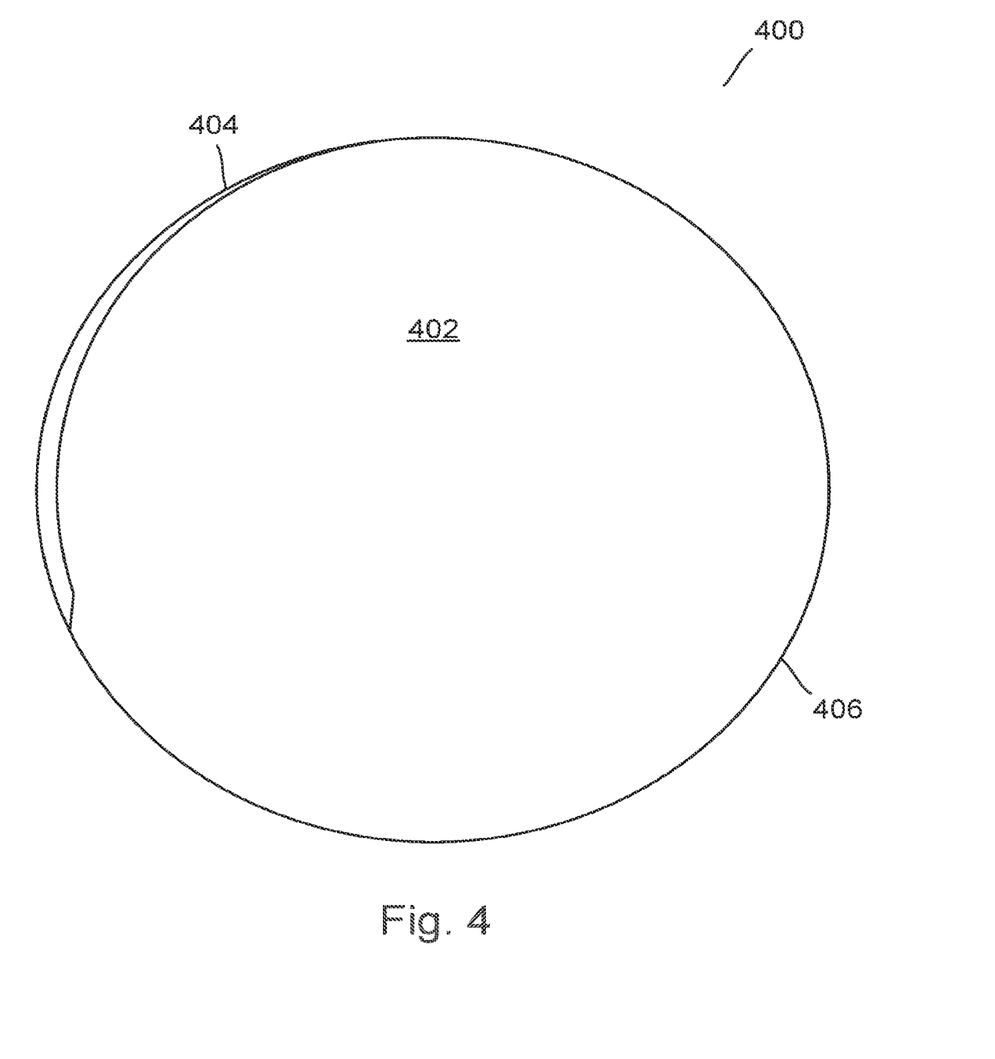
FIG. 4 illustrates another facial mask according to the disclosed embodiments.

FIG. 4 depicts another facial mask 400 according to the disclosed embodiments. As shown, facial mask 400 is round. Mask material 402 forms a round shape that includes foam sealer 404 glued or sewn onto a part of the mask. In some embodiments, foam sealer 404 is attached to an outer diameter of mask 400. Mask 400, for example, may fit around the head of a surgeon or other medical personnel with portion 406 against the back of the head. Foam sealer 404 form fits to the facial features of the user.

In other embodiments, facial mask 400 is a circular shape that fits over the mouth and nose area of the user. Foam sealer 404 rests against the face in a specified location Like the embodiments disclosed above, foam sealer 404 may include a wire or other means to form fit to the facial features. It also may be at the top of the circle shape to prevent the fogging of glasses.

Figure 5:
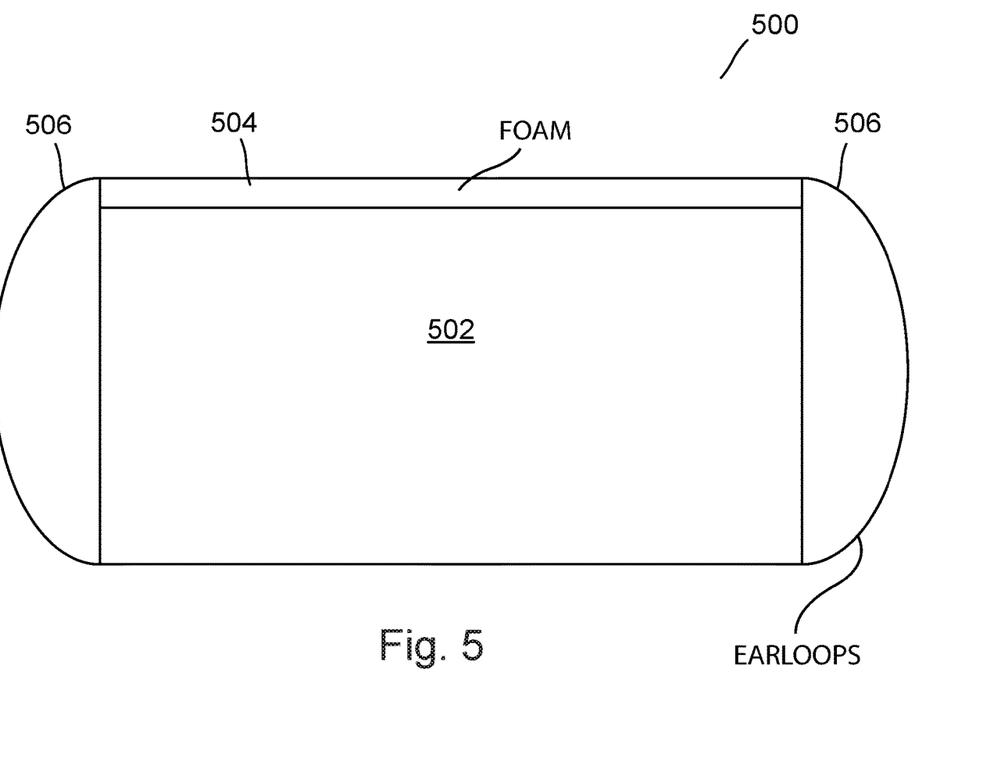
FIG. 5 illustrates another facial mask according to the disclosed embodiments.

FIG. 5 depicts another facial mask 500 according to the disclosed embodiments. Facial mask 500 may be similar in some aspects to mask 200 shown in FIGS. 2A and 2B, except that it includes ear loops 506. Facial mask 500 includes mask material 502 having a rectangular shape. Foam sealer 504 is attached to the top of the mask material. Foam sealer 504 may be glued or sewn onto the material. In other embodiments, another portion of the foam sealer may be attached to the "bottom" of mask material 502.

Facial mask 500 includes ear loops 506. Ear loops 506 may be comprised of stretchable material that extends away from mask material 502 to fit around the user's ears. Ear loops 506 hold mask 500 in place while foam sealer 504 deforms in accordance with the force applied by the ear loops. Ear loops 506 may be preferable when making a mask to fit many different types of users and head sizes. For example, ear loops 506 may be preferable for children. Further, ear loops 506 should not become undone during use.

FIG. 6 depicts a side view of a facial mask 600 having the foam sealers stitched therein according to the disclosed embodiments. Facial mask 600 may differ from previous masks in that the foam sealers do not use adhesive to attach to the mask material. Instead, the foam sealers are attached during the manufacturing process to the facial mask. This process may provide more stability for the foam sealers and less likelihood of separating from the mask material.

Facial mask 600 includes mask material 602. Foam sealers 604A and 604B also are included. Foam sealer 604A represents an upper boundary for facial mask 600. Sweat and materials from above the nose of a user may be kept from moving below foam sealer 604A. Breath is kept from rising above foam sealer 604A to prevent potentially fogging eyewear or causing other problems associated with known masks. Foam sealer 604B represents a lower boundary for facial mask 600. Saliva and other moisture are prevented from dropping below foam sealer 604B. Foam sealer 604B also may include an absorbent material to soak up saliva or sweat coming from the area inside facial mask 600 against the face of the user. Foam sealer 604B also blocks air, odors, and other materials from rising above it to enter the area enclosed by facial mask 600.

Facial mask 600 also include foam sealers 610. Foam sealers 610 are placed on the sides of the facial mask. Only one foam sealer is shown in FIG. 6, but another one may be on the opposite side. Foam sealers 610 also are comprised of open cell foam as well. The foam conforms to the face of a user in order to seal off the area inside mask 600 that touches the face. In some embodiments, foam sealers 610 extend the length between foam sealers 604A and 604B so that nothing escapes or gets into the area enclosed by facial mask 600. As shown in FIG. 6, facial mask 600 include vents 620 between foam sealers 604A and 604B and foam sealers 610. The upper vents 620 are located at each end of foam sealer 604A and the upper end of foam sealers 610, and the lower vents 620 are located at each end of foam sealer 604B and the lower end of foam sealers 610. Vents 620 may direct air in the form of breath to outside facial mask 600. Vents 620 direct the breathed air away from directly above facial mask 600 and not up to any eyewear. The lower vent of vents 620 may allow breathed air to escape downwards and away from the eyewear. Vents 620 also may allow some air inside the area covered by facial mask 600 to bring fresh air to the user.

Wires also may be incorporated within the foam sealers. Wire 608A is embedded in foam sealer 604A while wire 608B is embedded in foam sealer 604B. Foam sealers 610 includes embedded wires 608C. In some embodiments, only one foam sealer, such as foam sealer 604A, includes a wire. In other embodiments, the wires differ in terms of material and size. For example, wires 608C may not be as rigid as wires 604A and 604B. The diameters, for example, for wires 608C are smaller than for wires 604A and 604B. This feature allows one to move foam sealers 610 in order to let air escape from the area covered by facial mask 600. In other embodiments, wires 604A and 604B are bendable to fit with facial features of the user while wires 610 are not bendable.

Foam sealers 604A, 604B, and 610 are attached to mask material 602 by stitches 612. Stitches 612 are placed within mask material 602 and the foam sealers. Stitches 612 may secure the foam sealers in place so that they do not fall off facial mask 600. A specific stitching pattern may be used for stitches 612. In some embodiments, only one foam sealer is attached to mask material 602 by stitching. The other foam sealers may be attached using an adhesive, as disclosed above. This feature allows some variation in the configuration of facial masks 600. The user may attach foam sealers 610, for example, using an adhesive if desired. Preferably, at least foam sealer 604A is stitched onto mask material 602 using stitches 612. Stitches 612 may be comprised of threads of lightweight material.

In addition to stitches 612, facial mask 600 includes covers for the foam sealers. As facial mask 600 is manufactured with the foam sealers, it also may have them covered to provide more comfort to the user. Covers also may help with securing facial mask 600 to the face of the user. Covers 614A, 614B, and 614C are shown in FIG. 6. Cover 614A covers foam sealer 604A, cover 614B covers foam sealer 604B, and covers 614C cover foam sealers 610. The covers may completely enclose their respective foam sealers. Alternatively, the covers may include an opening on the ends to allow access to the foam sealer therein. The covers also may be made of the same material as mask material 602. If made of different material, then the covers may be comprised of something more durable than mask material 602.

Facial mask 600 also include ties 606. The upper set of ties 606 may be secured to upper border 616A and the lower set of ties secured to lower border 616B. Borders 616A and 616B provide extra stability to facial mask 600. Using the tension produced by ties 606, borders 616A and 616B may pull foam sealers 604A, 604B, and 610 inward towards the face of the user.

Figure 7:
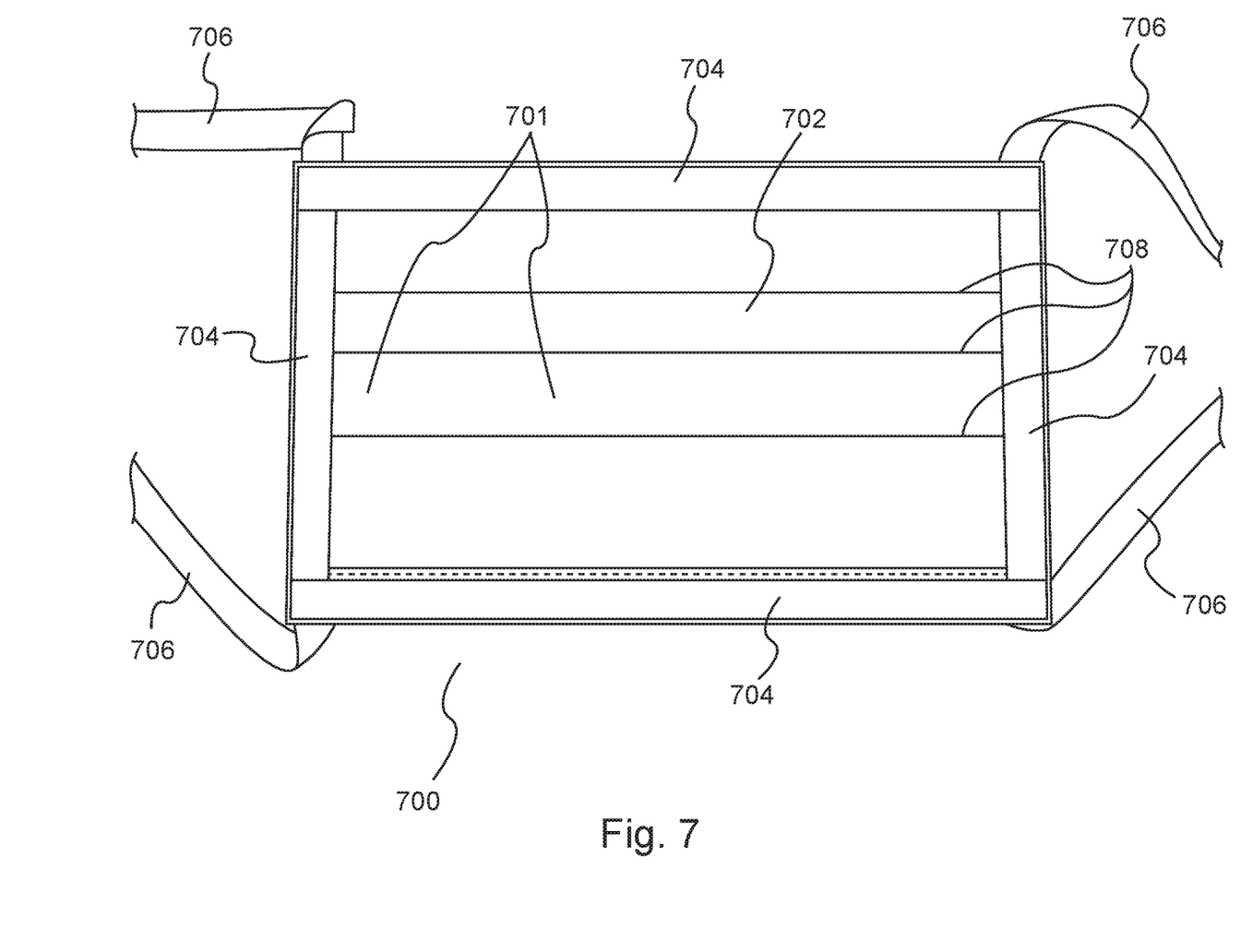
FIG. 7 illustrates a perspective view of a facial mask according to the disclosed embodiments.

FIG. 7 depicts a perspective view of a facial mask 700 according to the disclosed embodiments. Facial mask 700 may relate to facial mask 100 disclosed above. Facial mask 700 includes foam sealers 704 along the edges of the mask. The foam sealers may be glued or sewn onto the mask material. Mask material 702 also is shown with creases 708. Ties 706 are attached to the corners of facial mask 700. In this configuration, mask 700 prevents all materials and air from entering into area 701 shown for mask material. Area 701 is the part of facial mask 700 that covers the nose and mouth of the user. Foam sealers 704, however, seal area 701 off from outside materials and keeps mask material 702 off of the face and skin of the user.

Figure 8:
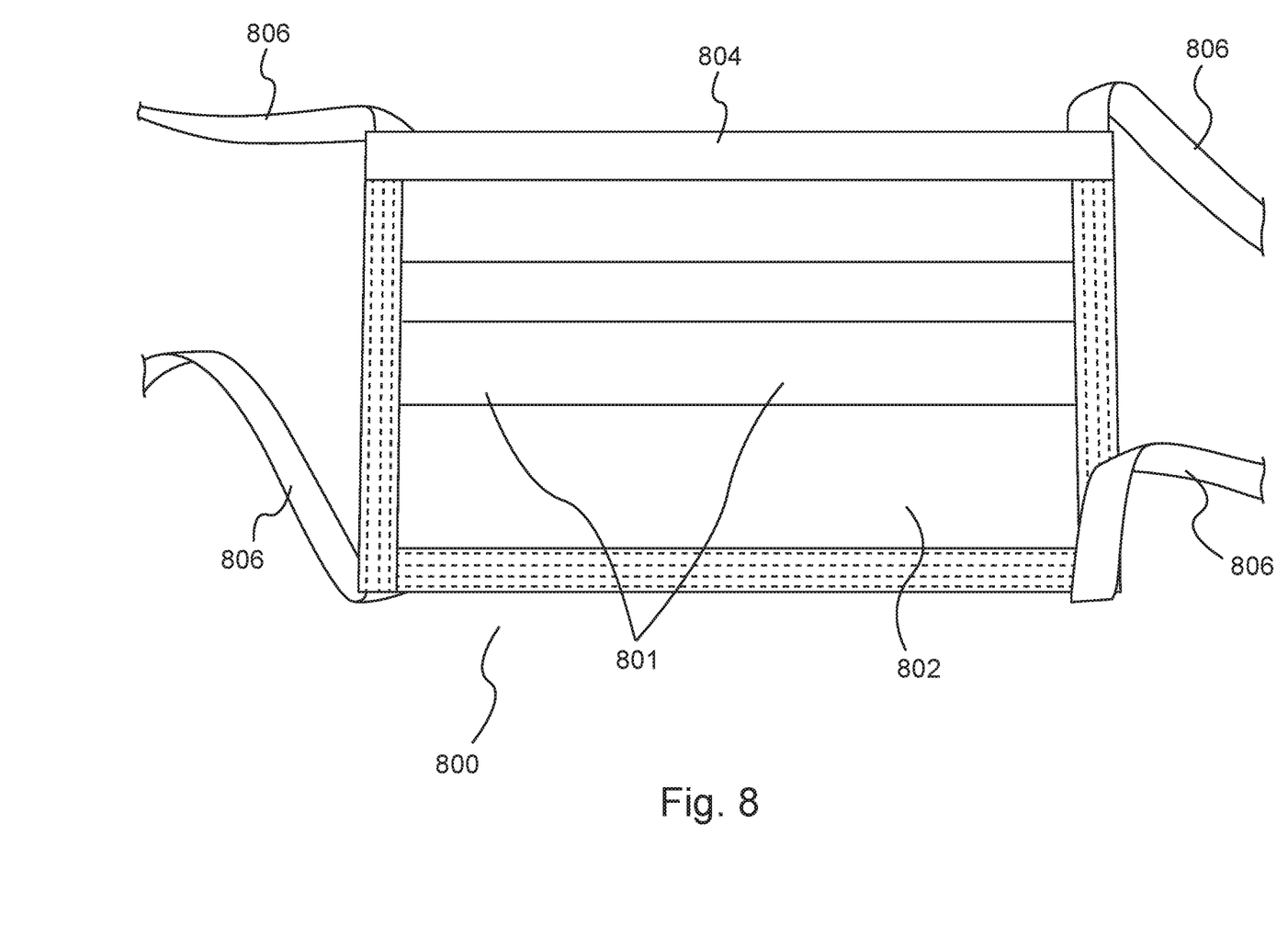
FIG. 8 illustrates another perspective view of a facial mask according to the disclosed embodiments.

FIG. 8 depicts a perspective view of a facial mask 800 according to the disclosed embodiments. Facial mask 800 may relate to facial mask 800 disclosed above. Facial mask 800 includes a foam sealer 804 along the top edge of the mask. Facial mask 800 also includes ties 806. Masks 700 and 800 include ties, though ear loops also may be used, as disclosed above. A wire may be embedded in foam sealer 804 to provide extra stability and formability. The wire may be bent to accommodate the shape of the nose of the user.

Facial mask 800 is comprised of mask material 802. Mask material 802 may contact the skin of the user. Thus, mask material 802 may differ to mask material 702 of facial mask 702. Material that does not contact the skin of the user by virtue of the foam sealers may be comprised of different material with various properties that are meant to keep air out of the face of the user. Facial mask 800 also includes area 801 that is the mask material covering the nose and mouth of the user.

Figure 9:
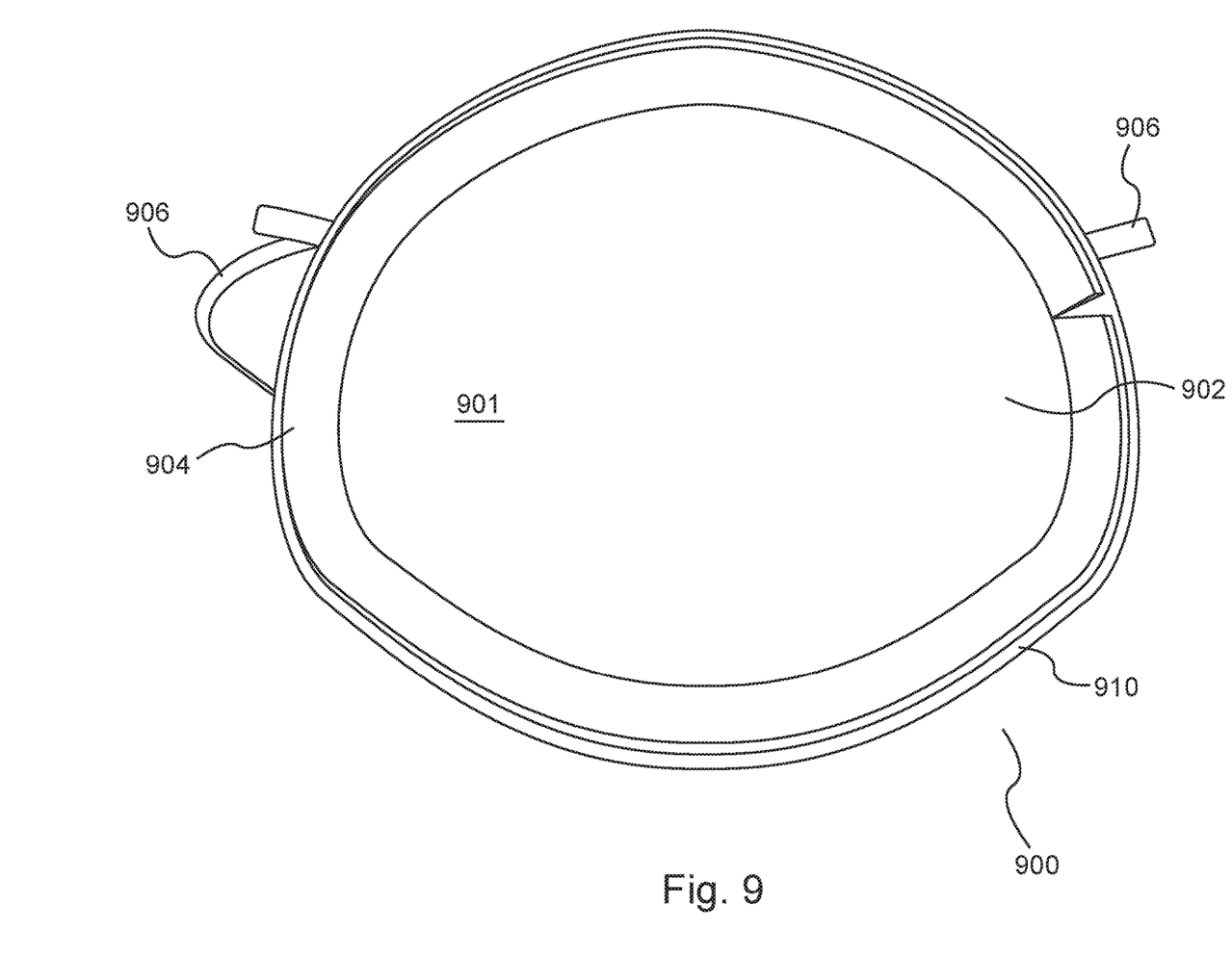
FIG. 9 illustrates another perspective view of a facial mask according to the disclosed embodiments.

FIG. 9 depicts a perspective view of a facial mask 900 according to the disclosed embodiments. Facial mask 900 may relate to facial mask 300 disclosed above. As shown in FIG. 9, facial mask 900 includes a foam sealer 904 positioned around the edge of the opening of the mask. Facial mask 900 also appears to include ear loops 906. A padding 910 may be placed between the foam sealer portions and the mask material.

Facial mask 900 also includes area 901 formed by foam sealer 904, padding 910, and mask material 902. Area 901 extends outwardly away from the face of the user. Area 901 accounts for the shape of the nose and mouth in this configuration. Foam sealer 904 may be sewn or stitched onto padding 910. Padding 910 allows facial mask 900 to expand or contract as needed. Alternatively, foam sealer 904 is attached using an adhesive to padding 910 or mask material 902.

Thus, the disclosed embodiments include a facial mask that improves over known masks by using a medical grade foam portion that attaches to the mask material. The foam portion, or sealer, may comprise open cell foam. It also may use medical grade adhesive to attach the foam sealer to the mask materials. Other embodiments may have the foam sealer sewn onto the mask material. The disclosed embodiments may apply to all shapes and sizes of masks. The foam sealer is on some part of the mask depending on the type of mask and level of protection/sealing needed.

It will be apparent to those skilled in the art that various modifications to the disclosed embodiments may be made without departing from the spirit or scope of the invention. Thus, it is intended that the present invention covers the modifications and variations disclosed above provided that these changes come within the scope of the claims and their equivalents.

The invention claimed is:

1. A facial mask comprising:
   mask material having a shape, wherein the mask material includes sides to form the shape;
   a foam sealer of open cell foam attached to a perimeter of the mask material, wherein the foam sealer is die cut to fit the mask material, the foam sealer comprising a pair of horizontal foam sealers and a pair of vertical foam sealers;
   stitches to attach the foam sealer to the mask material; and ties extending from two vertical sides of the sides of the mask material;
   a wire embedded in the foam sealer, wherein the wire is bent into a shape matching the foam sealer;
   a vent located between each end of the pair of horizontal foam sealers and each end of the pair of vertical foam sealers; and a cover overlapping the foam sealer; wherein the foam sealer consists of reticulated polyurethane foam having a fungicidal or bactericidal additive.

2. The facial mask of claim 1, wherein the shape is configured to accommodate a facial characteristic of a user.

3. The facial mask of claim 1, further comprising a padding between the foam sealer and the mask material.

4. A facial mask consisting of comprising:
   mask material having a shape formed by a plurality of sides;
   a plurality of foam sealers, wherein each foam sealer of the plurality of the plurality of foam sealers consists of open cell foam and is attached to each side of the plurality of sides of the mask material with stitches, the plurality of foam sealers comprising a pair of horizontal foam sealers and a pair of vertical foam sealers that include a vent between each end of each of the plurality of foam sealers;
   wherein the plurality of foam sealers are configured to have a shape corresponding to the shape of the mask material, and
   wherein each of the plurality of foam sealers include a bendable embedded wire;
   a plurality of covers, wherein each cover is attached to the mask material to enclose each of the plurality of foam sealers; and
   ties extending from vertical sides of the plurality of sides of the mask material;
   wherein each of the plurality of foam sealers consists of reticulated polyurethane foam having a fungicidal or bactericidal additive.

5. The facial mask of the claim 4, wherein at least one of the foam sealers is configured into the shape of a rectangle.

6. The facial mask of claim 4, wherein at least one of the foam sealers is configured into the shape of a circle.

7. A facial mask comprising:
   a first side and a second side as well as a top side and a bottom side,
   each side having mask material having a shape, wherein the mask materials are joined to form an opening enclosed by the first side and the second side;
   each side having a foam sealer of open cell foam attached by stitches to secure each of the foam sealers to the mask material at the border of the opening, each end of each of the foam sealers separated by a vent;
   each side having a strip that hangs below each of the foam sealers; and
   a bottom positioned opposite the opening, wherein the bottom is shorter in length than the opening; and a cover to enclose each foam sealer, wherein the cover extends away from the mask material;
   wherein each foam sealer consists of reticulated polyurethane foam having a fungicidal or bactericidal additive; and wherein each foam sealer includes a bendable embedded wire.

8. The facial mask of claim 7, wherein each of the foam sealers are heavier than the mask material.

\* \* \* \* \*